United States Patent [19]

Wagner et al.

[11] Patent Number: 5,234,896
[45] Date of Patent: Aug. 10, 1993

[54] HERBICIDAL 7-CHLORO-BENZOTHIAZOLYLOX-YACETAMIDES

[75] Inventors: Klaus Wagner, Cologne; Heinz Förster, Wuppertal; Robert R. Schmidt, Bergisch Gladbach; Hans-Joachim Santel, Leverkusen, all of Fed. Rep. of Germany

[73] Assignee: Bayer Aktiengesellschaft, Leverkusen, Fed. Rep. of Germany

[21] Appl. No.: 868,802

[22] Filed: Apr. 15, 1992

[30] Foreign Application Priority Data

Apr. 25, 1991 [DE] Fed. Rep. of Germany ..... 41134721

[51] Int. Cl.$^5$ ................... A01N 43/78; C07D 277/68
[52] U.S. Cl. ..................................... 504/267; 548/165
[58] Field of Search ............... 548/159, 171, 165; 71/90; 546/198, 146; 540/603; 504/267

[56] References Cited

U.S. PATENT DOCUMENTS 4,509,971 4/1985 Forster et al. ............... 71/90
4,784,682 11/1988 Forster et al. ............... 71/88
5,081,256 1/1992 Arnold et al. ............... 548/159

*Primary Examiner*—Patricia L. Morris
*Attorney, Agent, or Firm*—Sprung, Horn, Kramer & Woods

[57] ABSTRACT

Herbicidal 7-chloro-benzothiazolyloxyacetamides of the formula

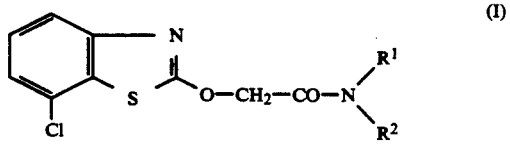

(I)

in which
R$^1$ represents hydrogen or an optionally substituted radical from the series comprising alkyl, alkenyl, alkinyl or aralkyl,
R$^2$ represents an optionally substituted radical from the series comprising alkyl, alkenyl, alkinyl, cycloalkyl, cycloalkenyl, aralkyl, aryl, alkoxy, alkenyloxy or alkinyloxy, or
R$^1$ and R$^2$, together with the nitrogen atom to which they are bonded, form an optionally substituted, saturated or unsaturated nitrogen heterocycle, which can contain further heteroatoms and to which a benzo group can be fused.

3 Claims, No Drawings

HERBICIDAL 7-CHLORO-BENZOTHIAZOLYLOXYACETAMIDES

The invention relates to new 7-chloro-benzothiazolyloxy-acetamides, to a process for their preparation and to their use as herbicides.

It has already been disclosed that certain benzothiazolyloxyacetamides, such as, for example, N-methyl-benzothiazolyloxyacetanilide and N-methyl-6-chloro-benzothiazolyloxyacetanilide have herbicidal properties (cf. EP-A 5501 and EP-A 161,602). However, the herbicidal activity of these compounds is not always entirely satisfactory.

New 7-chloro-benzothiazolyloxyacetamides have now been found, of the general formula (I)

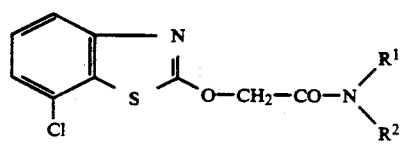

(I)

in which
R$^1$ represents hydrogen or an optionally substituted radical from the series comprising alkyl, alkenyl, alkinyl or aralkyl,
R$^2$ represents an optionally substituted radical from the series comprising alkyl, alkenyl, alkinyl, cycloalkyl, cycloalkenyl, aralkyl, aryl, alkoxy, alkenyloxy or alkinyloxy, or
R$^1$ and R$^2$, together with the nitrogen atom to which they are bonded, form an optionally substituted, saturated or unsaturated nitrogen heterocycle, which can contain further heteroatoms and to which a benzo group can be fused.

It has further been found that the new 7-chloro-benzothiazolyloxyacetamides of the formula (I) are obtained when 2,7-dichloro-benzothiazole of the formula (II)

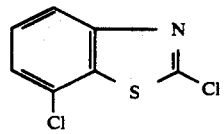

(II)

is reacted with hydroxyacetamides of the general formula (III)

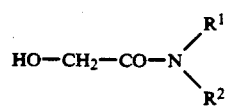

(III)

in which
R$^1$ and R$^2$ have the abovementioned meanings,
if appropriate in the presence of a diluent, if appropriate in the presence of an acid-binding agent and if appropriate in the presence of a catalyst.

Finally, it has been found that the new 7-chloro-benzo-thiazolyloxyacetamides of the formula (I) have interesting herbicidal properties.

Surprisingly, the compounds of the formula (I) according to the invention exhibit, together with very good tolerability to crop plants, such as, for example, rice, substantially stronger action against weeds which are difficult to control, such as, for example, cockspur grass, than N-methylbenzothiazolyloxyacetanilide and N-methyl-6-chloro-benzothiazolyloxyacetanilide, which are chemically obvious known compounds.

The invention preferably relates to compounds of the formula (I) in which
R$^1$ represents hydrogen, C$_1$-C$_8$-alkyl which is optionally substituted by fluorine, chlorine, cyano or C$_1$-C$_4$-alkoxy, C$_2$-C$_8$-alkenyl which is optionally substituted by fluorine and/or chlorine, C$_2$-C$_8$-alkinyl or benzyl,
R$^2$ represents C$_1$-C$_8$-alkyl which is optionally substituted by fluorine, chlorine, cyano or C$_1$-C$_4$-alkoxy, C$_2$-C$_8$-alkenyl which is optionally substituted by fluorine and/or chlorine, C$_2$-C$_8$-alkinyl, C$_3$-C$_6$-cycloalkyl which is optionally substituted by chlorine and/or C$_1$-C$_4$-alkyl, C$_5$- or C$_6$-cycloalkenyl, benzyl which is optionally substituted by fluorine, chlorine and/or C$_1$-C$_4$-alkyl, phenyl which is optionally substituted by fluorine, chlorine, bromine, iodine, cyano, nitro, C$_1$-C$_4$-alkyl, trifluoromethyl, C$_1$-C$_4$-alkoxy and/or C$_1$-C$_4$-alkylthio, C$_1$-C$_8$-alkoxy which is optionally substituted by C$_1$-C$_4$-alkoxy, or C$_3$-C$_4$-alkenyloxy, or
R$^1$ and R$^2$, together with the nitrogen atom to which they are bonded, form a saturated or unsaturated five- to seven-membered nitrogen heterocycle which is optionally benzo-fused and optionally mono- to trisubstituted by C$_1$-C$_3$-alkyl.

The invention relates in particular to compounds of the formula (I) in which
R$^1$ represents C$_1$-C$_4$-alkyl, allyl or propargyl,
R$^2$ represents C$_1$-C$_6$-alkyl, C$_1$-C$_2$-alkoxy-C$_1$-C$_2$-alkyl, allyl, propargyl, cyclopentyl, cyclohexyl, cyclo-hexenyl, benzyl, phenyl (which is optionally substituted by fluorine, chlorine, bromine, cyano, nitro, methyl, ethyl, trifluoromethyl, methoxy or ethoxy), C$_1$-C$_6$-alkoxy or C$_1$-C$_2$-alkoxy-C$_1$-C$_2$-alkoxy, or
R$^1$ and R$^2$, together with the nitrogen atom to which they are bonded, represent piperidinyl which is optionally mono- to trisubstituted by methyl and/or ethyl, pyrrolidinyl which is optionally mono- or disubstituted by methyl and/or ethyl, perhydroazepinyl or 1,2,3,4-tetrahydro(iso)-quinolinyl. Examples of the compounds o the formula (I) according to the invention are listed in Table 1 below.

TABLE 1

Examples of the compounds of the formula (I)

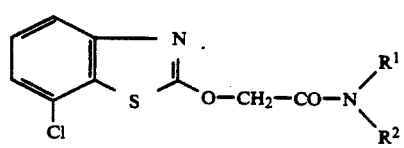

(I)

—N(CH$_3$)$_2$
—N(C$_2$H$_5$)$_2$
—N(C$_3$H$_7$)$_2$
—N(C$_4$H$_9$)$_2$
—N(CH$_2$CH=CH$_2$)$_2$
—N(CH$_2$C≡CH)$_2$

TABLE 1-continued

Examples of the compounds of the formula (I)

(I) Structure: 2-chloro-6-(N)-phenyl-S-C(=N)-O-CH₂-CO-N(R¹)(R²)

$-N(R^1)(R^2)$ groups:

- $-N(CH_3)(CH(CH_3)CH_2CH_3)$ — i.e., $-N$ with $CH_3$ and $CHC_2H_5$ (with $CH_3$)
- $-N(CH_3)(CH_2OCH_3)$
- $-N(CH_3)(\text{cyclohexyl, H})$
- $-N(CH_3)(\text{cyclohex-1-enyl})$
- $-N(CH_3)(\text{cyclohex-3-enyl})$
- $-N(CH_3)(CH_2CF_3)$
- $-N(CH_3)(CH_2C{\equiv}CH)$
- $-N(CH(CH_3)_2)(OCH_2CH_2OC_2H_5)$
- $-N{\langle}$ pyrrolidine $\rangle$ TABLE 1-continued Examples of the compounds of the formula (I)

(I) Structure: 2-chloro-6-(N)-phenyl-S-C(=N)-O-CH₂-CO-N(R¹)(R²)

$-N(R^1)(R^2)$ groups:

- $-N{\langle}$ 2-methylpyrrolidine $\rangle$
- $-N{\langle}$ piperidine $\rangle$
- $-N{\langle}$ 2-methylpiperidine $\rangle$
- $-N{\langle}$ 4-methylpiperidine $\rangle$
- $-N{\langle}$ 3,5-dimethylpiperidine $\rangle$
- $-N{\langle}$ 3-ethylpiperidine $\rangle$
- $-N{\langle}$ 2-ethylpiperidine $\rangle$
- $-N{\langle}$ 1,2,3,4-tetrahydroisoquinoline $\rangle$
- $-N{\langle}$ 3-methylpiperidine $\rangle$ TABLE 1-continued
Examples of the compounds of the formula (I)
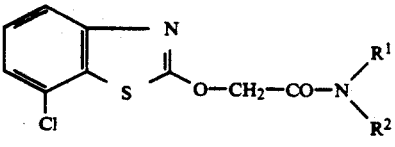
| $-N\diagdown_{R^2}^{R^1}$ |
|---|
| 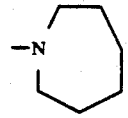 |
| 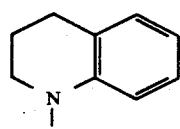 |
| 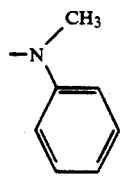 |
| 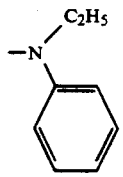 |
| 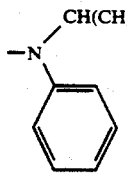 |
| 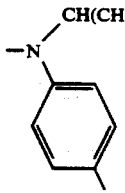 |
| 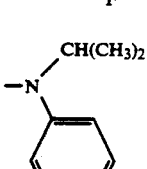 |
TABLE 1-continued
Examples of the compounds of the formula (I)
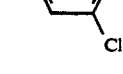
| $-N\diagdown_{R^2}^{R^1}$ |
|---|
|  |
| 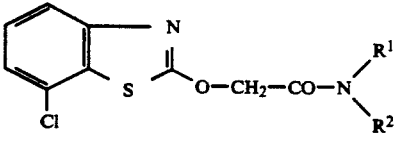 |
| 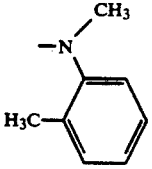 |
| 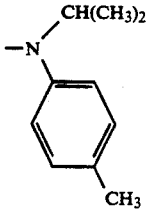 |
| 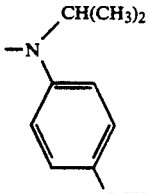 |
| 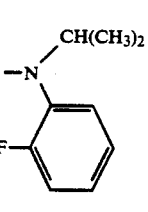 |

TABLE 1-continued

Examples of the compounds of the formula (I)

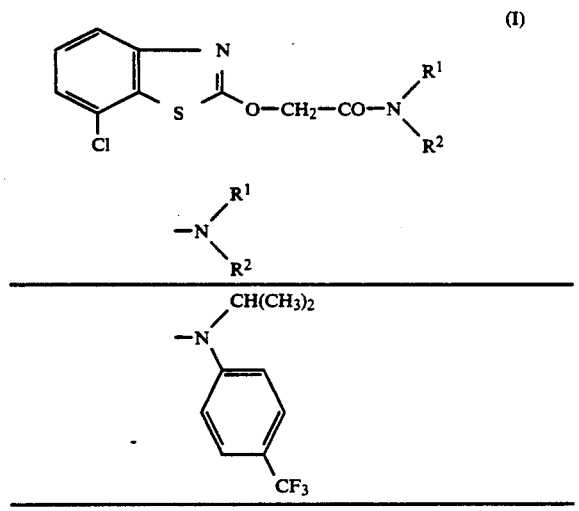

If, for example, 2,7-dichloro-benzothiazole and N,N-di-ethylhydroxyacetamide are used as starting substances, the course of the reaction in the preparation process according to the invention can be represented by the following equation:

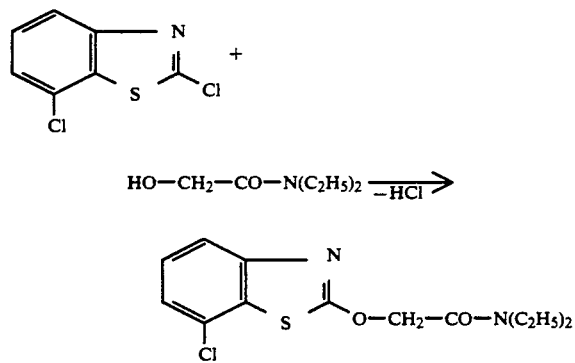

The 2,7-dichloro-benzothiazole of the formula (II) required as a starting substance in the preparation process according to the invention for the compounds of the formula (I) is already known (cf. Canad. J. Chem. 49 (1971), 956–964).

Formula (III) provides a general definition of the hydroxyacetamides further to be used as starting substances in the process according to the invention for the preparation of compounds of the formula (I).

In formula (III), $R^1$ and $R^2$ preferably or in particular have those meanings which have already been indicated above as preferred or as particularly preferred for $R^1$ and $R^2$ in connection with the description of the compounds of the formula (I) according to the invention.

The hydroxyacetamides of the formula (III) are known and/or can be prepared by processes known per se (cf. U.S. Pat. No. 4,509,971 and U.S. Pat. No. 4,645,525; furthermore U.S. Pat. No. 4,334,073, DE-OS (German Published Specification) 3,038,598, DE-OS (German Published Specification) 3,038,636, EP-A 37,526, EP-A 348,737, DE-OS (German Published Specification) 3,819,477).

The process according to the invention for the preparation of the new 7-chloro-benzothiazolyloxyacetamides of the formula (I) is preferably carried out using diluents. These preferably include hydrocarbons, such as, for example, toluene, xylene or cyclohexane, halogenohydro-carbons, such as, for example, methylene chloride, ethylene chloride, chloroform or chlorobenzene, ethers, such as, for example, diethyl ether, dipropyl ether, diisopropyl ether, dibutyl ether, diisobutyl ether, glycol dimethyl ether, tetrahydrofuran and dioxane, alcohols, such as, for example, methanol, ethanol, propanol, isopropanol or butanol, ketones, such as, for example, acetone, methyl ethyl ketone, methyl isopropyl ketone and methyl isobutyl ketone, esters, such as, for example, methyl acetate and ethyl acetate, amides, such as, for example, dimethylformamide, dimethylacetamide and N-methyl-pyrrolidone, nitriles, such as, for example, acetonitrile and propionitrile, sulphoxides, such as, for example, dimethyl sulphoxide and also water or aqueous salt solutions.

Salts which are used here are preferably chlorides or sulphates of alkali metals or alkaline earth metals, such as, for example, sodium chloride, potassium chloride or calcium chloride. Sodium chloride is particularly preferred.

The process according to the invention is advantageously carried out using acid-binding agents. Those which are preferably used are strongly basic alkali metal and alkaline earth metal compounds, for example oxides, such as, for example, sodium oxide, potassium oxide, magnesium oxide and calcium oxide, hydroxides, such as, for example, sodium hydroxide, potassium hydroxide, magnesium hydroxide and calcium hydroxide and/or carbonates, such as, for example, sodium carbonate, potassium carbonate, magnesium carbonate and calcium carbonate.

The addition of 0.01 to 10% by weight (relative to employed glycolamide of the formula (III)) of a phase transfer catalyst may be advantageous in some cases. Examples of those catalysts which may be mentioned are: tetrabutylammonium chloride, tetrabutylammonium bromide, tributyl-methylphosphonium bromide, trimethyl-$C_{13}/C_{15}$-alkyl-ammonium chloride, dibenzyl-dimethyl-ammonium methylsulphate, dimethyl-$C_{12}/C_{14}$-alkyl-benzylammonium chloride, tetrabutylammonium hydroxide, 18-crown-6, triethylbenzylammonium chloride, trimethylbenzylammonium chloride and tetraethylammonium bromide.

The reaction temperatures can be varied within a substantial range in the process according to the invention. In general, the reaction is carried out at temperatures between $-50°$ C. and $+110°$ C., preferably at temperatures between $-20°$ C. and $+80°$ C.

The process according to the invention is in general carried out at normal pressure, but it can also be carried out at elevated or reduced pressure, for example between 0.1 and 10 bar.

To carry out the process according to the invention, 0.5 to 5 mol, preferably 0.8 to 1.5 mol, of hydroxyacetamide of the formula (III) are in general employed per mole of 2,7-dichloro-benzothiazole of the formula (II). The reaction components can be mixed together in any desired sequence. The reaction mixture is in each case stirred until the reaction is complete and worked up by customary methods.

The active compounds according to the invention can be used as defoliants, desiccants, agents for destroying broad-leaved plants and, especially, as weed-killers. By weeds, in the broadest sense, there are to be understood all plants which grow in locations where they are undesired. Whether the substances according to the invention act as total or selective herbicides depends essentially on the amount used.

The active compounds according to the invention can be used, for example, in connection with the following plants:

Dicotyledon weeds of the central: Sinapis, Lepidium, Galium, Stellaria, Matricaria, Anthemis, Galinsoga, Chenopodium, Urtica, Senecio, Amaranthus, Portulaca, Xanthirua, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver, Centaurea, Trifolium, Ranunculus and Taraxacum.

Dicotyledon cultures of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledon weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledon cultures of the genera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total combating of weeds, for example on industrial terrain and rail tracks, and on paths and squares with or without tree plantings. Equally the compounds can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cocoa plantations, soft fruit plantings and hopfields, on lawns, turf and pasture land, and for the selective combating of weeds in annual cultures.

The compounds of the formula (I) according to the invention are in particular suitable for the control of monocotyledon weeds in dicotyledon crops, and in some cases also in monocotyledon crops (such as, for example, in rice). They are in particular suitable for the control of harmful grasses (such as, for example, Echinochloa) in paddy rice.

The active compounds can be converted into the customary formulations, such as solutions, emulsions, wettable powders, suspensions, powders, dusting agents, pastes, soluble powders, granules, suspension-emulsion concentrates, natural and synthetic materials impregnated with active compound, and very fine capsules in polymeric substances.

These formulations are produced in a known manner, for example by mixing the active compounds with extenders, that is, liquid solvents and/or solid carriers, optionally with the use of surface-active agents, that is, emulsifying agents and/or dispersing agents and/or foam-forming agents.

In the case of the use of water as an extender, organic solvents can, for example, also be used as auxiliary solvents. As liquid solvents, there are suitable in the main: aromatics, such as xylene, toluene or alkyl-naphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water.

As solid carriers there are suitable: for example ammonium salts and ground natural minerals, such as kaolins, clays, talc, chalk, quartz, attapulgite, montmorillonite or diatomaceous earth, and ground synthetic minerals, such as highly disperse silica, alumina and silicates, as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; as emulsifying and/or foam-forming agents there are suitable: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as albumen hydrolysis products; as dispersing agents there are suitable: for example lignin-sulphite waste liquors and methylcellulose.

Adhesives such as carboxymethylcellulose and natural and synthetic polymers in the form of powders, granules or latexes, such as gum arabic, polyvinyl alcohol and polyvinyl acetate, as well as natural phospholipids, such as cephalins and lecithins, and synthetic phospholipids, can be used in the formulations. Further additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

For controlling weeds, the active compounds according to the invention, as such or in the form of their formulations, can also be used as mixtures with known herbicides, finished formulations or tank mixes being possible.

Suitable herbicides for the mixtures are known herbicides, such as, for example, 1-amino—6-ethylthio—3-(2,2-dimethylpropyl)—1,3,5—triazine—2,4(1H,3H)-dione (AMETHY-DIONE) or N-(2-benzothiazolyl)-N,N,-dimethyl-urea (META-BENZTHIAZURON) for combating weeds in cereals; 4-amino-3-methyl—6-phenyl—1,2,4-triazin—5(4H)-one (METAMITRON) for combating weeds in sugar beet, and 4-amino—6-(1,1-di-methylethyl) —3-methylthio—1,2,4-triazin—5(4H)-one (METRIBUZIN) for combating weeds in soya beans. Surprisingly, some mixtures also show synergistic action.

Mixtures with other known active compounds, such as fungicides, insecticides, acaricides, nematicides, bird repellants, plant nutrients and agents which improve soil structure, are also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomising or scattering.

The active compounds according to the invention can be applied either before or after emergence of the plants. They can also be incorporated into the soil before sowing.

The amount of active compound used can vary within a substantial range. It depends essentially on the nature of the desired effect. In general, the amounts used are between 20 and 2000 g of active compound per hectare of soil surface, preferably between 50 and 1000 g per ha.

The preparation and use of the active compounds according to the invention can be seen from the following examples.

PREPARATION EXAMPLES

EXAMPLE 1

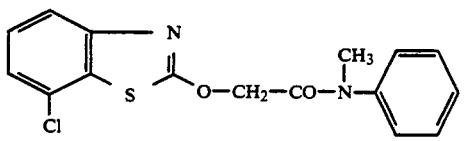

A mixture of 8.25 g (0.05 mol) of N-methylhydroxyacet-anilide, 3.1 g (0.05 mol of KOH) of 90% strength potassium hydroxide powder and 100 ml of isopropanol is cooled to −20° C. and a solution of 10.2 g (0.05 mol) of 2,7-di-chloro-benzothiazole in 40 ml of acetonitrile is added dropwise at this temperature with stirring. The reaction mixture is then stirred at 0° C. to 10° C. for 6 hours and then poured into 500 ml of water, and the product obtained in crystalline form is isolated by filtering with suction. 15.9 g (96% of theory) of N-methyl-(7-chloro-benzo-thiazol-2-yl-oxy)-acetanilide of melting point 114° C. are obtained.

The compounds of the formula (I)

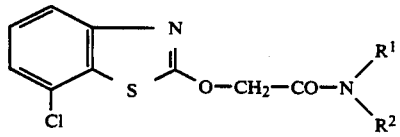

listed in Table 2 below can, for example, also be prepared analogously to Example 1 and in accordance with the general description of the preparation process according to the invention.

TABLE 2

| Preparation examples of the compounds of the formula (I) | | | |
|---|---|---|---|
| Ex. No. | $R^1$ | $R^2$ | Melting point (°C.) |
| 2 | $CH(CH_3)_2$ | phenyl | 106 |
| 3 | $CH(CH_3)_2$ | 4-F-phenyl | 105 |

TABLE 2-continued

| Preparation examples of the compounds of the formula (I) | | | |
|---|---|---|---|
| Ex. No. | $R^1$ | $R^2$ | Melting point (°C.) |
| 4 | $CH_3$ | 2-CH$_3$-phenyl | 126 |
| 5 | $CH_3$ | 3-CH$_3$-phenyl | 140 |
| 6 | $-CH_2-CH=CH_2$ | $-CH_2-CH=CH_2$ | 89 |
| 7 | $-(CH_2)_6-$ | | 102 |
| 8 | $n-C_4H_9$ | $n-C_4H_9$ | (oil) |
| 9 | $-CH_2-CH_2-CH(CH_3)-CH_2-CH_2-$ | | 96 |
| 10 | $-CH_2-CH=CH_2$ | $-CH=CH-CH_3$ | 57 |
| 11 | $CH_3$ | 2,3-(CH$_3$)$_2$-phenyl | 138 |
| 12 | $-CH=CH-CH_3$ | $-CH=CH-CH_3$ | (oil) |

Use Examples

The compounds shown below are used as comparison substances in the following use examples:

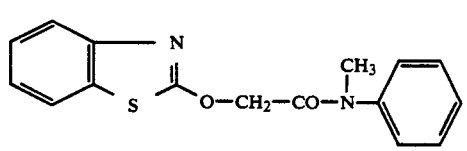

N-methylbenzothiazol−2-yl-oxy-acetanilide (disclosed in EP™ A 5501, Ex. 1);

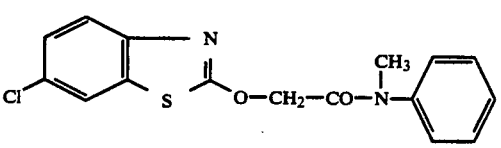

N-methyl-(6-chloro-benzothiazol−2-yl-oxy)-acetanilide (disclosed in EP-A 161,602, Ex. 1).

Example A

Pre-emergence water surface treatment with transplanted paddy rice

To produce a preparation which can be applied, 1 part of active compound is dissolved using 5 parts of acetone; 1 part of benzyloxy-polyglycol ether is then added as an emulsifier. Water is then added to the desired concentration. Rice in the 2-3 leaf stage is transplanted into pots which are filled with soil. Seeds of test plants are sown (1 cm deep). Two days later, the pots are covered 3 cm with water. The active compound preparations are then applied to the water surface. 4 weeks later, the herbicidal action and the damage to the treated plants is evaluated visually in % in comparison with untreated plants. 0% denotes no action, 100% denotes complete dying-off.

In this test, the very good compatibility of the active compounds according to the invention—in particular of the compound from Preparation Example 1—in rice together with substantially stronger action against weeds, in particular against cockspur grass (Echinochloa crus galli), in comparison with the known compounds (A) and (B) is seen.

made without departing from the spirit and scope of the present invention.

We claim:

1. N-methyl-(7-chloro-benzothiazol-2-yl-oxy)-acetanilide of the formula

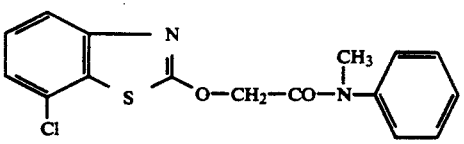

2. A herbicidal composition comprising a herbicidally effective amount of a compound according to claim 1 and a diluent.

3. A method of combating unwanted vegetation which comprises applying to such vegetation or to a locus from which it is desired to exclude such vegetation a herbicidally effective amount of a compound according to claim 1.

TABLE A

| Active compound | Application rate (g/ha) | % Action on transplanted rice | Damage to Echinochloa |
|---|---|---|---|
| (A) (known) | 500 | 0 | 100 |
|  | 250 | 0 | 90 |
|  | 125 | 0 | 70 |
| (B) (known) | 500 | 0 | 100 |
|  | 250 | 0 | 80 |
| (1) | 500 | 0 | 100 |
|  | 250 | 0 | 100 |
|  | 125 | 0 | 100 |

It will e appreciated that the instant specification and claims are set forth by way of illustration and not limitation, and that various modifications and changes may be

UNITED STATES PATENT AND TRADEMARK OFFICE
CERTIFICATE OF CORRECTION

PATENT NO. : 5,234,896
DATED : August 10, 1993
INVENTOR(S) : Wagner, et al.

It is certified that error appears in the above-identified patent and that said Letters Patent is hereby corrected as shown below:

Title Page  [30] Foreign Application Priority Data: Delete " 41134721 " and substitute -- 4113421 --

Signed and Sealed this

Tenth Day of January, 1995

Attest:

BRUCE LEHMAN

*Attesting Officer*  *Commissioner of Patents and Trademarks*